United States Patent [19]
Bornzin et al.

[11] Patent Number: 5,643,338
[45] Date of Patent: Jul. 1, 1997

[54] SINGLE-PASS A-V LEAD FOR PACING WITH STIMULATION OF RIGHT VENTRICULAR OUTFLOW TRACT

[75] Inventors: Gene A. Bornzin, Simi Valley; Brian M. Mann, Beverly Hills, both of Calif.

[73] Assignee: Pacesetter, Inc., Sylmar, Calif.

[21] Appl. No.: 629,959

[22] Filed: Apr. 3, 1996

[51] Int. Cl.$^6$ .................................................. A61N 1/05
[52] U.S. Cl. ............................................ 607/123; 607/125
[58] Field of Search ................................. 607/116, 119, 607/122, 123, 125, 126; 128/642

[56] References Cited

U.S. PATENT DOCUMENTS

| | | |
|---|---|---|
| 4,154,247 | 5/1979 | O'Neill . |
| 4,393,883 | 7/1983 | Smyth et al. . |
| 4,402,329 | 9/1983 | Williams . |
| 4,497,326 | 2/1985 | Curry . |
| 4,567,901 | 2/1986 | Harris . |
| 4,602,645 | 7/1986 | Barrington et al. . |
| 4,627,439 | 12/1986 | Harris . |
| 4,643,201 | 2/1987 | Stokes . |
| 4,664,120 | 5/1987 | Hess . |
| 4,711,027 | 12/1987 | Harris . |

OTHER PUBLICATIONS

JACC, vol. 21, No. 2, Feb. 1993, 328A Abstract 803–1; Revaluation of The Optimal Pacing Site; Septrum or Apex.
JACC, vol. 21, No. 2, Feb. 1993, 328A Abstract 803–2; Permanent Right Ventricular Outflow Tract Pacing Improves Cardiac Output.
JACC, vol. 21, No. 2, Feb. 1993, 328A Abstract 803–6; Effect of Contraction Sequence On Left Ventricular Function And Wall Motion.
NASPE 1992, Pace vol. 15, Part II Apr. 1992, p. 511, Abstract 25; Assessment of Left Ventricular Function in Relation to Electrode Position: Effects of Left Ventricular Outflow Tract Pacing.

*Primary Examiner*—Jeffrey R. Jastrzab

[57] ABSTRACT

A single-pass A-V lead for cardiac pacing comprises a lead body having an atrial electrode and a right ventricular outflow tract (RVOT) electrode. Preformed bends in the lead body are configured such that the atrial and RVOT electrodes are biased against walls of the right atrium and the RVOT respectively. Biasing forces generated by the preformed bends help to maintain the atrial and RVOT electrodes in their respective positions following implantation. The lead advantageously permits ventricular stimulation in the RVOT, resulting in an improved sequence of ventricular activation and a corresponding increase in cardiac output. Branched and unbranched embodiments of the lead are disclosed.

35 Claims, 7 Drawing Sheets

SINGLE-PASS A-V LEAD FOR PACING WITH STIMULATION OF RIGHT VENTRICULAR OUTFLOW TRACT

FIELD OF THE INVENTION

This invention relates to electrical leads for cardiac pacing. In particular, this invention relates to single-pass A-V leads that permit the atrial and ventricular electrodes to be positioned and held at desirable locations within the heart.

BACKGROUND OF THE INVENTION

In a normally functioning heart, the sino-atrial (S-A) node generates electrical signals that control the contractions of the heart. These signals are generally in the form of quasi-periodic voltage impulses that are of sufficient magnitude to cause the contraction of the heart muscle. In a single cycle of the heart, a signal (i.e., a voltage impulse) is generated by the S-A node, causing the right and left atria to contract. The contractions of the right and left atria force blood into the corresponding right and left ventricles. The signal is also conducted through the AV node to the right and left ventricles (after a short time delay), causing the right and left ventricles to contract.

Various disorders in the cardiac electrophysiological system can cause abnormalities in the rate and/or the timing of the contractions of the heart. For example, a malfunctioning AV node conduction system can delay or prevent the transmission of the signal to the right and left ventricles, impairing or preventing the stimulation of the ventricles. Such disorders can often be corrected by use of a cardiac pacemaker.

Cardiac pacing involves the electrical stimulation of the heart in order to control the timing of the contractions of the heart. Electrical stimuli in the form of pulses are generated by a battery-powered pacemaker and applied to the tissue of the heart by one or more electrodes that are connected to the pacemaker via flexible, insulated conductors. The electrical stimuli supplement or supersede the electrical signals generated by the S-A node. The insulated conductors and associated electrodes form what is referred to as the "lead." The electrode (or electrodes) of a lead may also be used to sense intrinsic electrical activity within the heart.

For endocardial leads that stimulate the inner walls or "endocardium" of the heart, implantation is typically performed by inserting the distal end of the lead into the patient's cephalic vein (one of the main veins from the upper arm), and forwarding the distal end through the subclavian vein and superior vena cava into the right side of the heart. Once the lead is properly positioned (using fluoroscopy to view the distal end of the lead), the proximal end of the lead is connected to the pacemaker and the pacemaker is implanted beneath the skin.

For various disorders it is desirable to pace the heart by applying separate electrical stimuli to the atrium and the ventricle of the right side of the heart. This form of pacing, commonly known as dual chamber pacing, generally requires the placement of an atrial electrode in the right atrium and a ventricular electrode in the right ventricle. In addition to applying electrical stimuli to the tissue of the respective chambers, one or both of these electrodes may be used to sense intrinsic electrical activity, and to thereby detect timing abnormalities. For example, the pacemaker may sense the naturally-occurring electrical activity in the right atrium and use this information to generate appropriate electrical stimuli to apply to the right ventricle.

One problem with dual chamber pacing involves the need to separately position and maintain the atrial and ventricular electrodes in contact with the electrically-sensitive tissue of the respective chambers. The use of separate atrio and ventricular leads permits the independent manipulation and positioning of the atrial and ventricular electrodes. However, the need to pass two separate leads complicates the implantation procedure.

To solve this problem, various designs have been proposed which include both the atrial and ventricular electrodes on a single lead. These types of leads are generally referred to as single-pass atrio-ventricular (A-V) leads.

One type of single-pass A-V lead has a lead body that separates into an atrial branch and a ventricular branch in the vicinity of the heart, with each branch having an electrode at its distal tip. (See, for example, U.S. Pat. No. 4,567,901 to Harris; U.S. Pat. No. 4,643,201 to Stokes; and U.S. Pat. No. 4,393,883 to Smyth et al.) The atrial branch extends into the right atrium, projecting the atrial electrode against the tissue of the right atrium. The ventricular branch similarly extends into the right ventricle, projecting the ventricular electrode against the tissue of the right ventricle (typically in the region of the ventricular apex, as discussed below). One or both branches may be preformed to assume a bent position following implantation. Such bends assist the proper positioning of the electrodes within the atrium and ventricle.

Another type of single-pass A-V lead has both electrodes on a single, unbranched lead body, with the ventricular electrode located at the distal tip of the lead body and the atrial electrode spaced above the distal tip on the lead body. (See Harris U.S. Pat. No. 4,711,027; O'Neill U.S. Pat. No. 4,154,247; and Curry U.S. Pat. No. 4,497,326.) One or more preformed bends in the atrial portion of the lead body may be used to maintain the atrial electrode in contact with the atrial tissue.

With both types of single-pass A-V leads described above, one or more hollow channels or "lumens" may be provided to permit the temporary insertion of one or more relatively stiff guidewires or "stylets" into the lead. When inserted, a stylet maintains the prebent portions of the lead (or the branches of the lead) through which the stylet passes in a substantially straight, but bendable, configuration, facilitating implantation. Upon withdrawal of the stylet (once the distal end of the lead is positioned within the heart), the prebent portions of the lead assume their curved or bent configurations. These bends help to position the electrodes so that they contact the tissue of the respective chambers at desirable locations.

When pacing the heart, it is generally desirable to contact the most electrically sensitive areas of tissue. Contact with such areas permits the use of pulses of lower amplitude and/or pulse width in comparison with the less electrically sensitive areas of the heart. It is also desirable to position the electrodes in areas where they are not likely to dislodge following implantation. The risk of the electrodes dislodging is especially high during the first few hours following implantation, before fibrous tissue of the heart walls forms around the electrodes.

Existing single-pass A-V leads are typically designed to place the ventricular electrode in the right ventricular apex. The ventricular apex has a concave bottom surface that is well suited for holding an electrode in a stable position. Further, the tissue of the right ventricular apex has been found to be suitable for the stimulation and sensing of the right ventricle.

Research with single-electrode leads has shown, however, that stimulation high in the right ventricle, in the region of the right ventricular outflow tract (RVOT), may produce a higher cardiac output. The RVOT is a region high in the right ventricle and below the pulmonary valve. Stimulation within the RVOT, or high along the interventricular septum, is believed to produce a better sequence of activation. The sequence of activation refers to the spread of the electrical signal from it's point of application through the muscle, and the muscular contraction that results from the spread. In comparison to stimulation in the apex, stimulation in the region of the RVOT has been found to produce a more rapid sequence of activation (or QRS sequence), resulting in faster ventricular contractions and improved cardiac output.

Unfortunately, the walls of the RVOT are generally vertical, and are not well suited for the stable placement of a ventricular electrode by conventional methods. Electrode placement in the RVOT is particularly challenging with single-pass A-V leads, wherein both atrial and ventricular electrodes must be maintained in position with a single lead. Accordingly, there is a need for a single-pass A-V lead that is suitable for positioning and maintaining a ventricular electrode in the RVOT.

SUMMARY OF THE INVENTION

The present invention relates to a single-pass A-V lead that includes a means for positioning and maintaining a ventricular electrode within the RVOT. The lead enables dual chamber cardiac pacing with ventricular stimulation in the RVOT. Stimulation in the RVOT produces in an improved sequence of ventricular activation, and thereby increases cardiac output.

The lead preferably comprises a flexible lead body that has at least one preformed portion that is configured so as to bias a ventricular electrode against a wall of the RVOT. The lead has at least one lumen that extends axially from an exit port at the proximal end of the lead through the lead body. The lumen is adapted for the insertion of a relatively stiff stylet. The stylet holds the preformed portion (or portions) of the lead body in a substantially straight configuration when fully inserted, permitting implantation through the venous system.

Once the stylet is withdrawn from the lumen, the preformed portion (or portions) of the lead body generates biasing forces that bias the atrial and ventricular electrodes against walls of the right atrium and RVOT respectively. The walls of the RVOT are generally vertical, and not well suited for holding an electrode in a stable position by conventional methods. This problem is overcome by the generation of the biasing forces, which are sufficient to maintain the ventricular electrode in a stable position within the RVOT following implantation.

In one preferred embodiment of the lead, the lead body has an unbranched distal portion with a ventricular electrode (referred to herein as the "RVOT electrode") located at the distal tip and an atrial electrode formed in-line with the lead body and spaced proximally from the RVOT electrode. A single lumen extends from the exit port substantially to the distal tip of the lead body. The atrial portion of the lead body is preformed such that a laterally projecting bow forms in the atrial portion upon removal of the stylet. The bow laterally displaces the atrial electrode so that it presses against an atrial wall in a direction generally toward the RVOT. The ventricular portion of the lead body is preformed to assume a curved or looped configuration when the stylet is removed. The preformed atrial and ventricular portions are configured relative to one another such that the RVOT electrode moves generally upward and then laterally toward the atrial electrode as the stylet is withdrawn (i.e., the distal tip of the lead body and the laterally projecting portion of the bow generally come together).

When the distal portion of the lead is properly positioned within the heart, the preformed ventricular portion of the lead body acts to position the RVOT electrode against the wall of the RVOT that is adjacent to the aorta (generally proximate to the right atrium), with the atrial electrode typically positioned against the interatrial septum. The tissue separating the RVOT and the right atrium is squeezed between the atrial and RVOT electrodes, and the distal portion of the lead does not reach the configuration that would be reached if the stylet were removed with the lead located in free space. The preformed bends in the atrial and ventricular portions of the lead body thus interact to produce generally opposite biasing forces that press the atrial and ventricular electrodes against generally opposite walls of the heart. The electrodes and the distal portion of the lead are thereby held in position.

In another embodiment, the lead is composed as described above, but includes a different combination of preformed bends in accordance with a different fixation technique. The atrial portion is preformed such that it forms a laterally projecting bow upon removal of the stylet. The bow is configured so that the atrial electrode presses against right atrial free wall. The ventricular portion is preformed to assume a curved configuration upon removal of the stylet, with the curve being configured so as to position the RVOT electrode against the interventricular septum (within the RVOT) upon removal of the stylet.

The atrial and ventricular portions are configured relative to one another so that the RVOT electrode curves upward and then laterally away from the atrial electrode (i.e., in the lateral direction opposite from the laterally projecting bow) as the stylet is removed. The right atrial free wall and the interventricular septum are sufficiently closely spaced to prevent the distal portion of the lead from reaching its relaxed, free space configuration. The preformed bends in the atrial and ventricular portions of the lead body thus generate biasing forces that press the electrodes against the respective walls of the heart. The electrodes and the distal portion of the lead are thereby held in position.

In yet another embodiment, the lead body has separate atrial and ventricular branches at the distal end of the lead, with the atrial electrode located at the distal tip of the atrial branch and the RVOT electrode located at the distal tip of the ventricular branch. Two separate lumens are provided. The first lumen extends from a first exit port at the proximal end of the lead substantially to the distal tip of the atrial branch. The second lumen extends from a second exit port at the proximal end of the lead substantially to the distal tip of the ventricular branch. The atrial branch is preformed to assume a generally J-shaped configuration upon removal of a first stylet from the first lumen. The ventricular branch is preformed to assume a generally J-shaped configuration upon removal of a second stylet from the second lumen.

The preformed atrial branch is configured so as to bias a portion of the lead body against the posterior wall of the superior vena cava while biasing the atrial electrode against the atrial appendage. This biasing force generated by the preformed atrial branch is sufficient to maintain the atrial branch position. The preformed ventricular branch is configured so as to hook the RVOT electrode into the RVOT and to bias the RVOT electrode against an RVOT wall which is generally proximate to the right atrium. The biasing forces applied by the atrial electrode against the atrial appendage and by the lead body against the posterior wall of the superior vena cava help to maintain the ventricular branch in position.

DETAILED DESCRIPTION OF THE PREFERRED EMBODIMENTS

FIGS. 1-12 illustrate three preferred embodiments of single-pass A-V leads (hereinafter "leads"). Each of the three leads is designed to position and maintain the ventricular electrode in the region of the RVOT, and to thereby enable dual chamber pacing with an improved sequence of ventricular activation. In accordance with this aspect of the present invention, the ventricular electrode of each lead design will hereinafter be referred to as the "RVOT electrode." As detailed below, each design uses a different combination of preformed bends to generate biasing forces that hold the atrial and RVOT electrodes in position.

The three illustrative leads shown and described are unipolar leads. However, as will be recognized by those skilled in the art, the inventive aspects of the present invention are equally applicable to bipolar single-pass A-V leads. Further, while the leads described herein use passive fixation type electrodes, it will be understood that such leads can easily be modified to use active fixation type electrodes without departing from the spirit of the invention.

Figure 1:
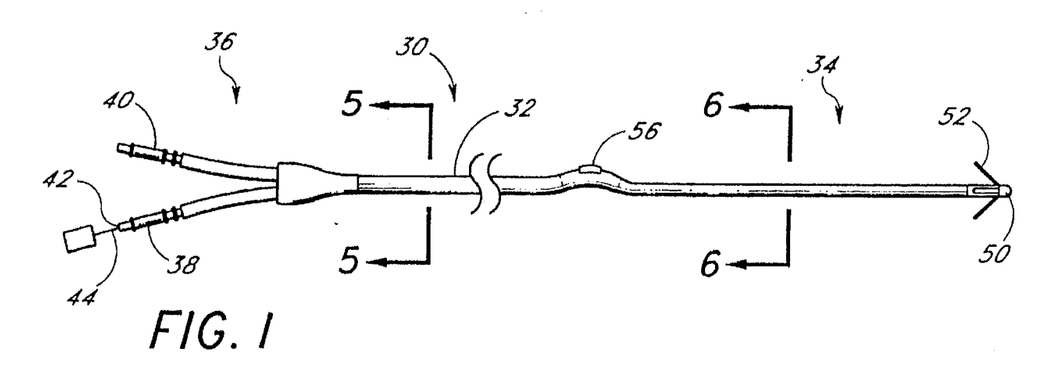
FIG. 1 is a plan view of an embodiment of a single-pass A-V lead in accordance with the present invention.

FIGS. 1-6 illustrate the first preferred embodiment. Referring to FIG. 1, a lead 30 comprises an elongated, insulated lead body 32 having a distal end 34 and a bifurcated proximal end 36. The lead 30 has first and second pin connectors 38, 40 that are adapted for connection to a pacemaker (not shown). The first connector 38 has a port 42 that is adapted for the insertion of a guidewire or "stylet" 44. A hollow channel or "lumen" 110 (FIGS. 4, 5 and 6) extends axially from the port 42 through the lead body 32 and into the distal end 34. The stylet 44 is shown in FIG. 1 in a fully inserted position, maintaining the lead body 32 in a substantially straight configuration (as is desirable for transvenous implantation).

An RVOT electrode 50 is located at the distal tip of the lead 30. The RVOT electrode 50 shown is a passive fixation type electrode, having flexible tines 52 to accommodate the growth of fibrous tissue around the electrode 50. However, as will be recognized by those skilled in the art, an active fixation type electrode that uses a retractable barb or screw to hold the electrode 50 in position could be used.

Spaced proximally from the RVOT electrode 50 and formed in-line with the lead body 32 is an atrial electrode 56. The atrial electrode 56 preferably has a curved configuration as shown. This curved configuration helps to maintain the atrial electrode 56 at an outermost portion of a bow 90 (FIGS. 2 and 3) that forms in the lead body 32 when the stylet 44 is removed.

Figure 2:
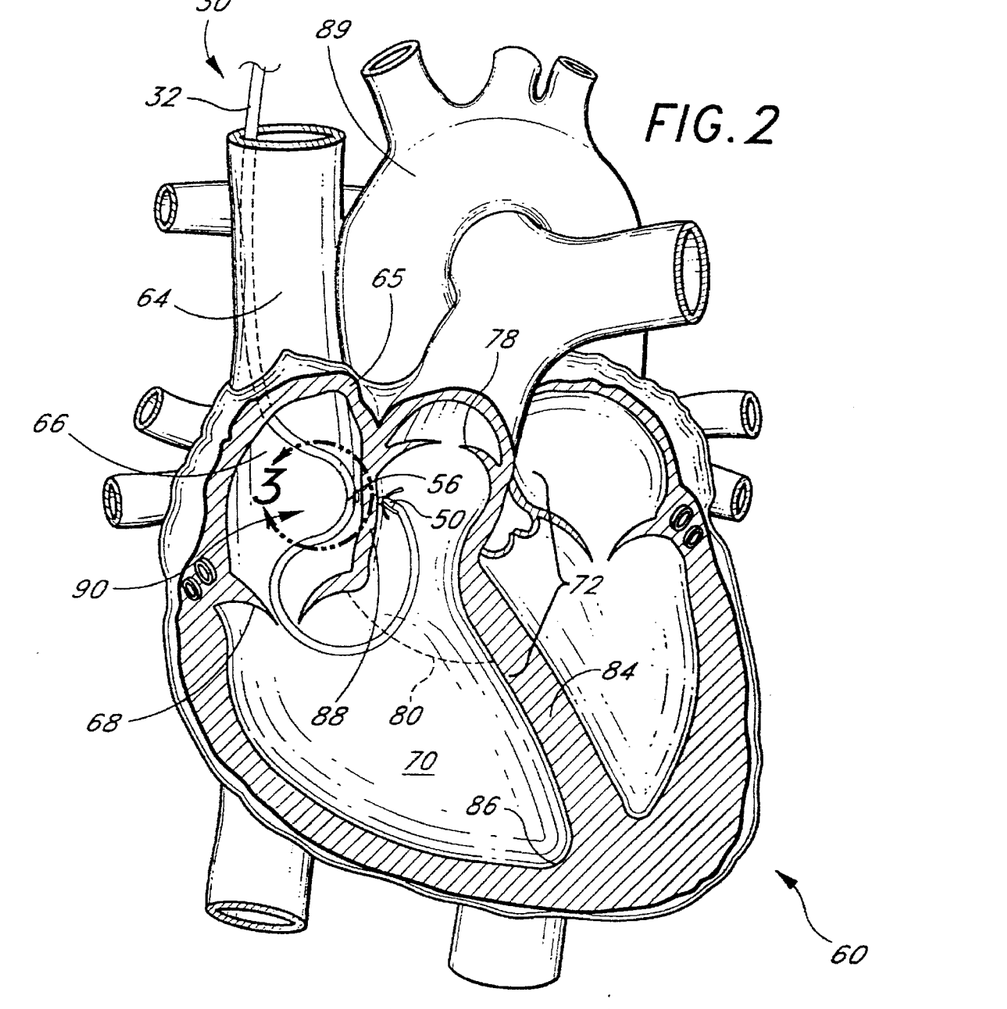
FIG. 2 is a perspective view illustrating the distal portion of the lead of FIG. 1 following implantation within a human heart.

FIG. 2 illustrates the distal portion of the lead 30 following proper implantation within a human heart 60. This figure best illustrates the configuration the lead 30 assumes once the stylet 44 has been withdrawn with the distal end 34 properly inserted within the heart 60. The lead 30 is shown as extending through the superior vena cava 64, into the right atrium 66, through the tricuspid valve 68, into the right ventricle 70, and into the RVOT 72. As used herein, the term RVOT 72 is defined as the region of the right ventricle 70 falling generally below the pulmonary valve 78 and above the dashed line 80, wherein the dashed line 80 intersects with the interventricular septum 84 approximately half way between the pulmonary valve 78 and the right ventricular apex 86. As will be recognized by those familiar with the anatomy of the heart, the lead 30 will extend anteriorly (i.e., toward the viewer) to some degree as it progresses from the superior vena cava 64 into the right ventricle 70.

Figure 3:
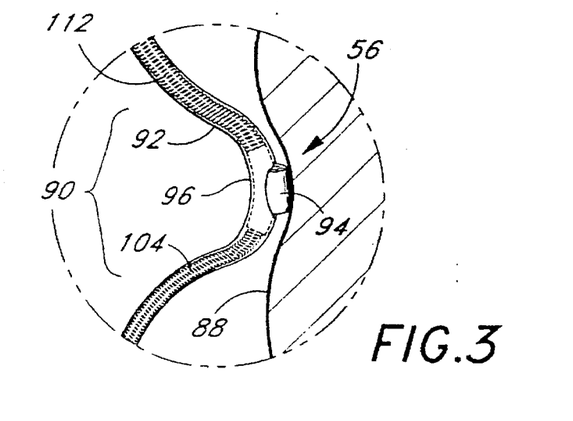
FIG. 3 is an enlarged view of the atrial electrode taken along the line 3—3 of FIG. 2.

Referring to FIGS. 2 and 3, the atrial portion of the lead body 32 (i.e., the portion that extends generally within the right atrium 66) is preformed or preshaped to form a laterally projecting bow 90 in the atrial lead portion upon removal of the stylet 44. The bow 90 displaces the atrial electrode 56 so that is presses against a wall 88 of the atrium 66, in the region of the atrial appendage 65 or the interatrial septum. (The interatrial septum is shown generally by reference number 88 in FIG. 2, but falls somewhat behind the RVOT 72). The atrial electrode 56 has a fixed curvature (as shown in FIG. 1). This curvature of the atrial electrode 56 helps to shape the bow 90, and further helps to maintain the atrial electrode 56 at the outermost portion of the bow 90. This ensures that the atrial electrode 56 contacts the wall 88 of the atrium 66, while keeping the insulated portion of the lead body 32 generally away from the heart tissue. The bow 90 is preferably configured such that the lead body 32 presses against the posterior wall of the superior vena cava 64, as shown in phantom in FIG. 2. This helps to force the atrial electrode 56 into position during implantation, and helps to bias the atrial electrode 56 in a direction generally toward the RVOT 72.

Referring to FIG. 3, a protrusion 94 of the electrode 56 extends outwardly in the direction of the bow 90, pressing against the atrial wall 88. The protrusion 94 helps to maintain good electrical contact with the atrial wall 88. The remaining portions of the electrode 56, including the inward-facing surface 96 (in the interior of the bow 90), are coated with an insulating layer 92 to minimize unnecessary discharge of electrical energy into the bloodstream (the coated portions of electrode 56 are shown in phantom). This reduction of discharge of energy and a concurrent reduction in current flow into the bloodstream increases the battery life of the pacemaker.

Referring again to FIG. 2, the ventricular portion of the lead body 32 (i.e., the portion generally shown within the right ventricle 70) is preformed to assume a curved configuration upon removal of the stylet 44. The resulting curve or loop is formed so as to project the RVOT electrode 50 against a wall of the RVOT 72 that is adjacent to the aorta 89, and generally proximate to the right atrium 66. As generally shown in FIG. 2, the RVOT electrode 50 is advantageously positioned substantially opposite from the atrial electrode 56.

The preformed bends in the atrial and ventricular portions of the lead body 32 interact with each other to produce substantially equal and opposite biassing forces that force the RVOT and atrial electrodes 50, 56 generally toward each other. These biasing forces cause the RVOT and atrial electrodes 50, 56 to effectively squeeze or pinch the heart tissue falling between the electrodes, and serve to hold the electrodes in position. (Although the cross-sectional view of FIG. 2 shows the electrodes as being separated by a single wall 88, it will be recognized by those skilled in the art that multiple adjacent walls of heart tissue may separate the electrodes 50, 56, depending upon the position of the lead 30 within the heart 60.) This method of holding the electrodes 50, 56 in position advantageously enables dual chamber pacing with stimulation of the RVOT 72.

Although the atrial bow 90 and the curved ventricular portion of the lead 30 are shown in FIG. 2 as falling generally within the same plane, the lead 30 may advantageously be constructed such that the these two prebent lead portions fall within different planes from one another. By constructing the lead 30 so that the atrial bow 90 falls generally within a first plane and so that the curved ventricular portion falls generally within a second plane that is rotated (preferably between 30 and 90 degrees) with respect to the first plane, the atrial electrode 56 can be selectively directed to different positions along the medial wall, near the fossa ovalis (not shown), or near the section of the right atrial wall that separates the right atrium 66 from the aorta 89. This construction facilitates electrode placement during implantation, and provides for improved stability of the atrial electrode 56 over the single-plane construction. This feature of the lead design is further described below with reference to FIGS. 7A and 7B, which illustrate two different planar orientations of the atrial bow 90 and the curved ventricular portion relative to one another.

Figure 4:
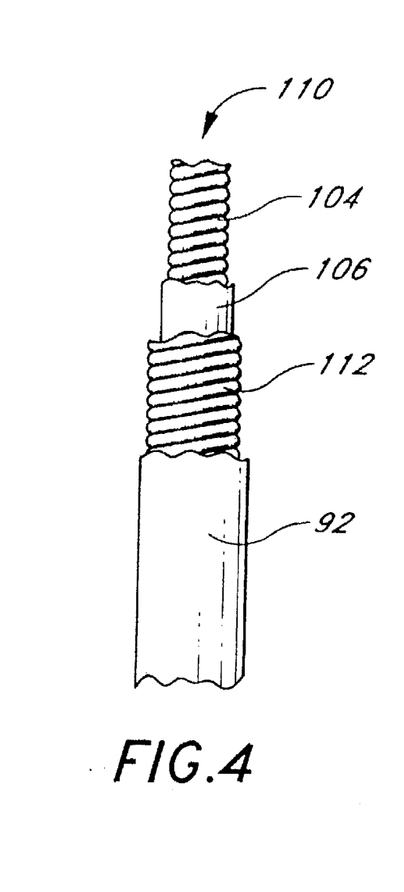
FIG. 4 is an elevational view of a portion of the lead of FIG. 1 with component parts thereof cut away to reveal its construction.
Figure 5:
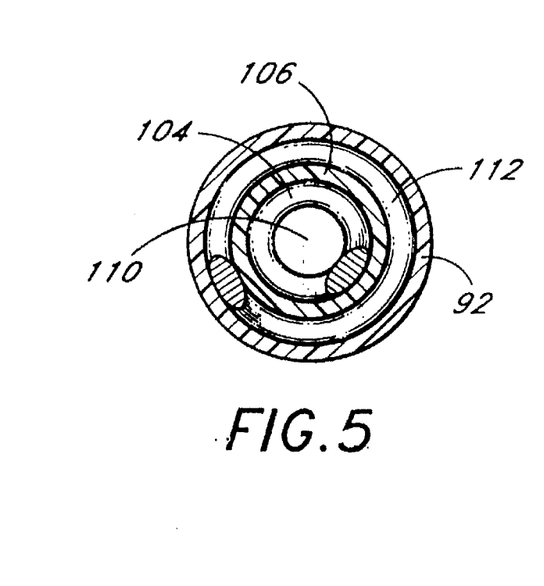
FIG. 5 is a cross-sectional view taken on the line 5—5 of FIG. 1.

FIGS. 4 and 5 illustrate the internal composition of the lead body 32 in the region between the bifurcated proximal portion 36 (FIG. 1) and the atrial electrode 56. An inner conductor 104 in the form of a helical coil is surrounded by an inner insulating layer 106. As best shown in FIG. 5, the inner walls of the inner conductor 104 form a lumen 110 through which the stylet 44 (FIG. 1) may be passed. The inner insulating layer 106 is surrounded by a second conductor 112 that is also in the form of a helical coil. The second conductor 112 is covered by the insulating layer 92.

The inner conductor 104 conductively connects the first pin connector 38 to the RVOT electrode 50. The outer conductor 112 conductively connects the second pin connector 40 to the atrial electrode 56. As best shown in FIG. 3, the inner conductor 104 and surrounding inner insulating layer 106 pass through a hollow central portion (not shown) of the atrial electrode 56.

Figure 6:
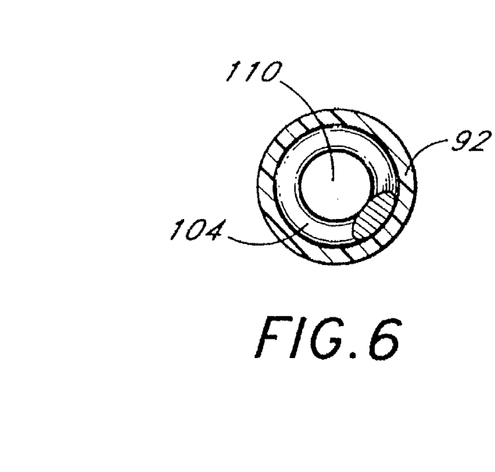
FIG. 6 is a cross-sectional view taken on the line 6—6 of FIG. 1.

FIG. 6 shows the internal composition of the ventricular portion of the lead body 32. The inner conductor 104 is surrounded by the insulating layer 92.

The above-described preformed bends in the atrial and ventricular portions of the lead body 32 are formed during the manufacture of the lead 30 using methods that are well known in the art. The bends may be molded into the insulating layers 92, 106, and/or may be formed in the helical-coil conductors 104, 112. The flexible nature of the helical-coil conductors 104, 112 and of the insulating layers 92, 106 permit the preformed portions of the lead body 32 to be held in substantially straight configurations when the relatively stiff stylet 44 inserted.

Figure 7A:
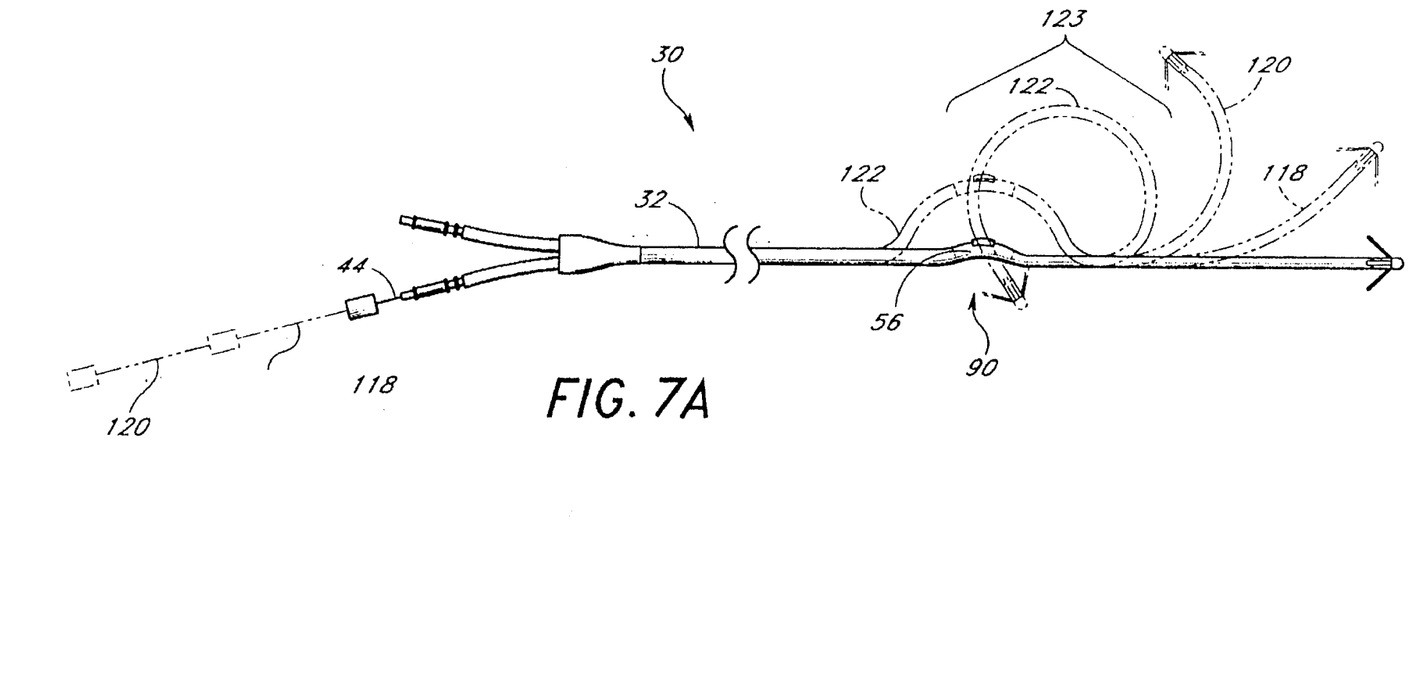
FIG. 7A is a plan view which illustrates, for one possible prebend construction of the lead of FIG. 1, the transformation in lead configuration as a stylet is withdrawn from a lumen that extends through the lead.

FIG. 7A illustrates, for a single-plane construction of the lead 30, the transformation in configuration that results as the stylet 44 is withdrawn from the lumen 110 with the lead 30 in free space. The reference numbers 118, 120 and 122 and corresponding phantom views illustrate lead body 32 configurations for progressive stages of stylet 44 withdrawal. Referring to the phantom view denoted by reference number 118, as the stylet 44 is withdrawn the ventricular portion of the lead body 32 begins to assume a curved configuration. Referring to the phantom view denoted by the reference number 120, the curvature of the ventricular portion increases as the stylet 44 is further withdrawn beyond the position indicated by reference number 118. For the phantom views denoted by reference numbers 118 and 120, the stylet 44 has not been fully withdrawn from the ventricular portion; thus, the atrial portion retains its initial configuration of FIG. 1.

The phantom view denoted by the reference number 122 illustrates the lead body 32 configuration following complete withdrawal of the stylet 44. As shown, the ventricular portion forms a complete loop 123, with the distal tip overlapping the lead body 32 in the region of the atrial electrode 56. (As generally shown in FIG. 2, the heart tissue separating the right atrium 66 from the RVOT 72 prevents this loop from closing when the lead 30 is positioned within the heart 60). Further, the bow 90 forms in the atrial portion of the lead.

Figure 7B:
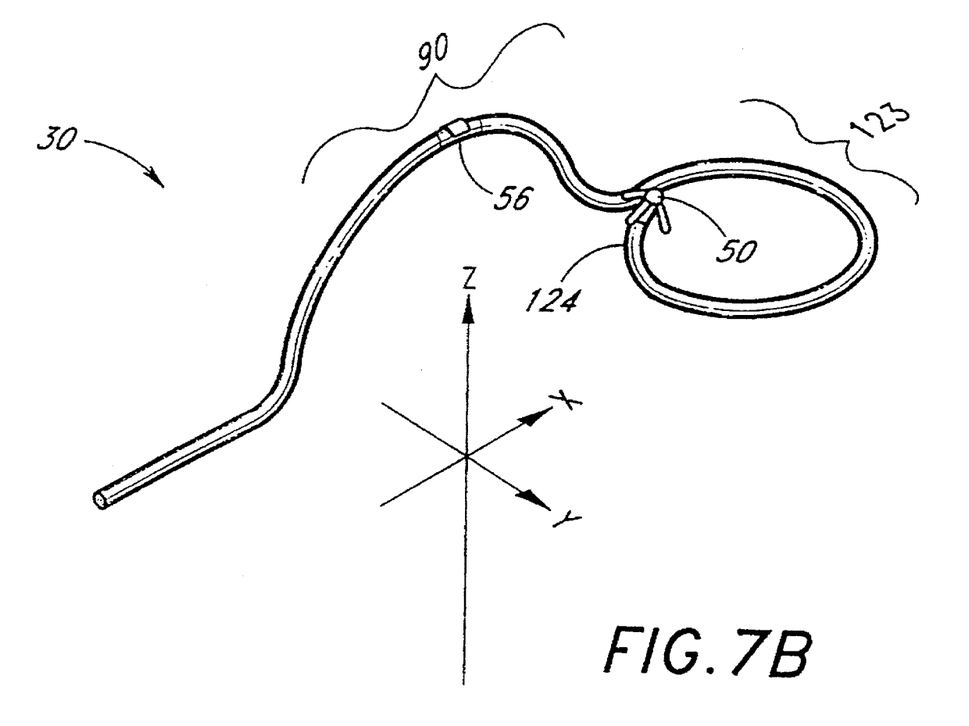
FIG. 7B is a perspective view which illustrates, for a second prebend construction of the lead of FIG. 1, the relaxed configuration of the distal portion of the lead when the stylet is withdrawn from the lumen.

As indicated above, the prebent portions of the lead 30 may alternatively be formed such that the atrial bow 90 falls generally within a first plane and the distal loop 123 falls generally within a second plane that is rotated (preferably between 30 and 90 degrees) with respect to the first plane. FIG. 7B illustrates such a prebend construction in which the angle of rotation between the atrial bow 90 and the distal loop 123 is approximately 90 degrees. In the embodiment shown in FIG. 7B, the atrial bow 90 falls generally within the XZ plane and the distal loop 123 falls generally within the XY plane. By varying the angle of rotation between the atrial bow 90 and the distal loop 123, the atrial electrode 56 can advantageously be directed to different positions along the medial wall. It is contemplated that leads of this type will be manufactured with different angles of rotation (between the bow 90 and the loop 123) to accommodate different medical conditions.

The embodiment of FIG. 7B also includes an inward bend 124 in the last 1.5 cm of the distal portion of the lead 30. This inward bend 124 projects the RVOT electrode 50 out of the XY plane in generally the positive Z direction. Preferably, the angle formed by the inward bend 124 is in the range of 30 to 90 degrees. When the lead 30 of FIG. 7B is implanted within the heart, the inward bend 124 serves to direct the RVOT electrode 50 toward the pulmonary valve 78 (FIG. 2). Implantation studies have shown that the incorporation of the inward bend 124 helps to bring the electrode 50 into stable contact with the tissue of the RVOT 72.

With reference to FIG. 2, it is contemplated that during the implantation process the physician will view the distal portion of the lead 30 on a fluoroscope as the stylet 44 is removed. This will allow the physician to view the rotational orientation of the atrial and ventricular portions within the heart 60, and to achieve the proper rotational orientation by rotating the lead 30 as necessary. A radio opaque marker (not shown) can be placed on the lead 30 to further assist the physician in viewing the rotational orientation. The lead 30 may also be partially inserted or withdrawn as the stylet 44 is removed to achieve proper placement of the RVOT and atrial electrodes 50, 56.

Figure 8:
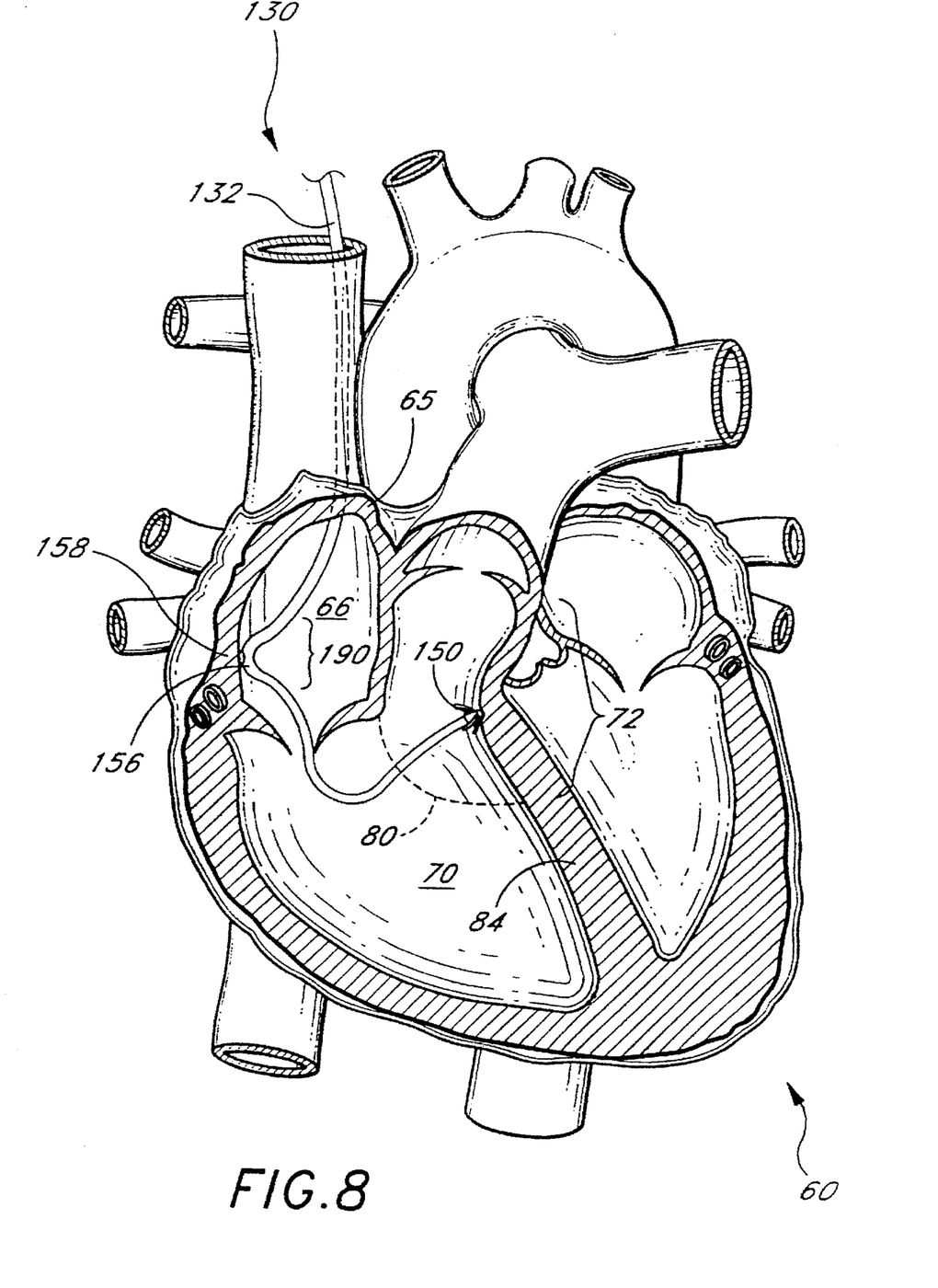
FIG. 8 is a perspective view of another embodiment of a single-pass A-V lead in accordance with the present invention following implantation within the heart.

FIG. 8 shows a second illustrative lead 130 in accordance with the present invention. The lead 130 is shown in FIG. 8 as implanted within a human heart 60. The lead 130 has a different combination of preformed bends than the lead 30 of FIGS. 1–7B, but is otherwise substantially identical to the lead 30. Accordingly, except for the configuration of the preformed bends, FIGS. 1 and 3—6 and the associated descriptions are applicable to the lead 130 of FIG. 8. The components and features of the lead 130 are denoted in FIG. 8 by the corresponding reference numbers used in FIGS. 1–7 preceded by the digit "1."

As shown in FIG. 8, the atrial portion of the lead body 132 is preformed so as to form a bow 190 when the stylet 44 (FIG. 1) is withdrawn. The bow 190 serves to project the curved, atrial electrode 156 against the right atrial free wall 158. The ventricular portion of the lead body 132 is preformed to assume a curved configuration upon withdrawal of the stylet 44, with the direction of curvature being generally opposite the direction of the bow 190. The curve in the ventricular portion serves to project the RVOT electrode 150 against the interventricular wall 84 within the RVOT 72. The curvature of the ventricular portion can be modified (during manufacture) from the curvature shown in FIG. 8 to place the RVOT electrode at a different location along the interventricular wall 84.

The preformed bends in the atrial and ventricular portions interact to produce generally equal and opposite biasing forces that urge the atrial and RVOT electrodes 156, 150 away from each other. When the lead 130 is implanted as shown in FIG. 8, these biasing forces push the electrodes 156, 150 against respective inner walls of the heart, maintaining the electrodes 156, 150 in their respective positions.

The transformation in the configuration of the lead body 132 as the stylet 44 is withdrawn is generally similar to that shown in FIG. 7, except that the lead body 132 progresses toward the configuration shown in FIG. 8 as the stylet 44 is withdrawn. To obtain proper electrode placement during implantation, it is contemplated that the RVOT electrode 150 will be positioned (using fluoroscope) with the stylet 44 withdrawn from the ventricular portion but inserted through the atrial portion. Once the RVOT electrode 150 has been positioned, the stylet 44 will be withdrawn from the atrial portion to expand the horizontal distance between the electrodes 150, 156, to thereby secure the electrodes 150, 156 and the distal portion of the lead 130 in position.

FIGS. 9–12 show a third illustrative lead 230 in accordance with the present invention. In contrast to the leads 30 and 130 described above which have unbranched distal portions, the lead 230 has separate, preformed atrial and ventricular branches.

Figure 9:
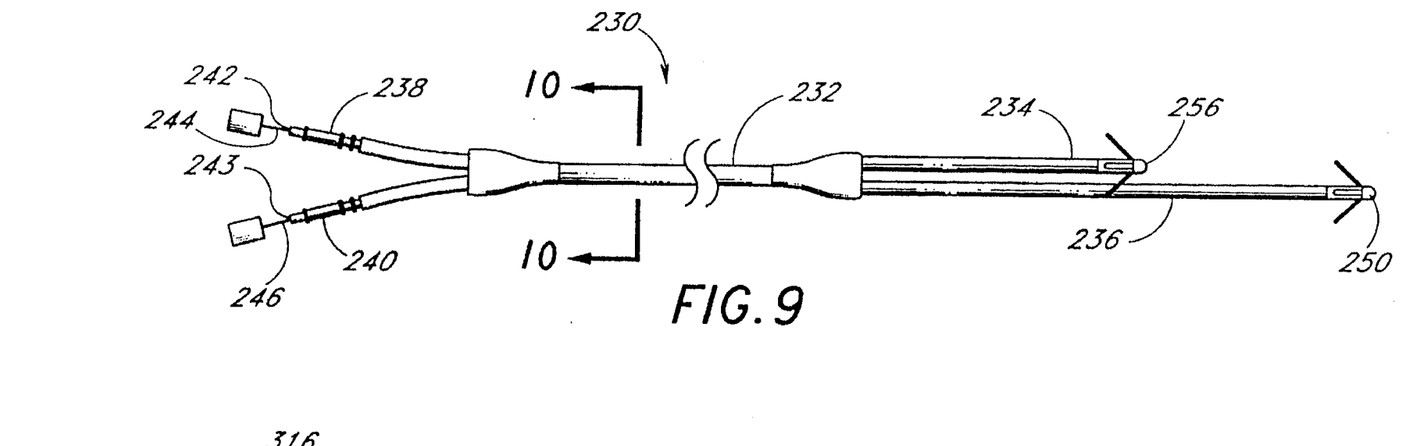
FIG. 9 is a plan view of yet another embodiment of a single-pass A-V lead in accordance with the present invention.

Referring to FIG. 9, the lead 230 comprises a lead body 232 that has an atrial branch 234 and a ventricular branch 236 at the distal end of the lead. The lead 230 further comprises first and second pin connectors 238, 240 at its proximal end. Each pin connector 238, 240 has a port 242, 243 adapted for the insertion of a stylet 244, 246. The stylets 244, 246 are shown in FIG. 9 as fully inserted, maintaining the lead body 232 (including the atrial and ventricular branches 234, 236) in a substantially straight configuration.

The ventricular branch 236 has an RVOT electrode 250 located at its distal tip. The atrial branch 234 similarly has an atrial electrode 256 located at its distal tip. The electrodes 250, 256 shown are passive fixation type electrodes such as the electrode 50 (FIGS. 1 and 2) described above.

Figure 10:
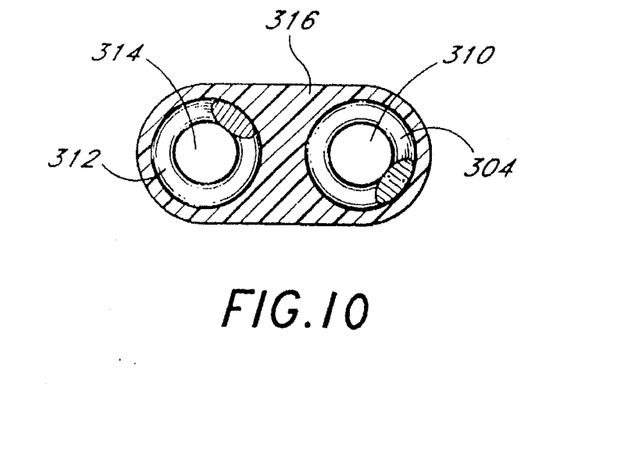
FIG. 10 is a cross-sectional view taken on the line 10—10 of FIG. 9.

As shown in FIG. 10, a first conductor 304, in the form of a helical coil, defines a first lumen 310 by its inner surface. A second conductor 312, also in the form of a helical coil, defines a second lumen 314 by its inner surface. The first and second conductors 304, 312 are spaced apart, and are surrounded by an insulating layer 316. The lumens 310, 314 are adapted for the insertion of the stylets 244, 246. Cross-sections of the atrial and ventricular branches 234, 236 are not shown, and are substantially the same as the cross-section shown in FIG. 6.

Referring to FIGS. 9 and 10, the first conductor 304 conductively connects the first pin connector 238 to the atrial electrode 256. The corresponding lumen 310 extends from the port 242 through the lead body 232 and into the atrial branch 234. The second conductor 312 conductively connects the second pin connector 240 to the ventricular electrode 256. The corresponding lumen 314 extends from the port 243 through the lead body 232 and into the ventricular branch 236.

Figure 11:
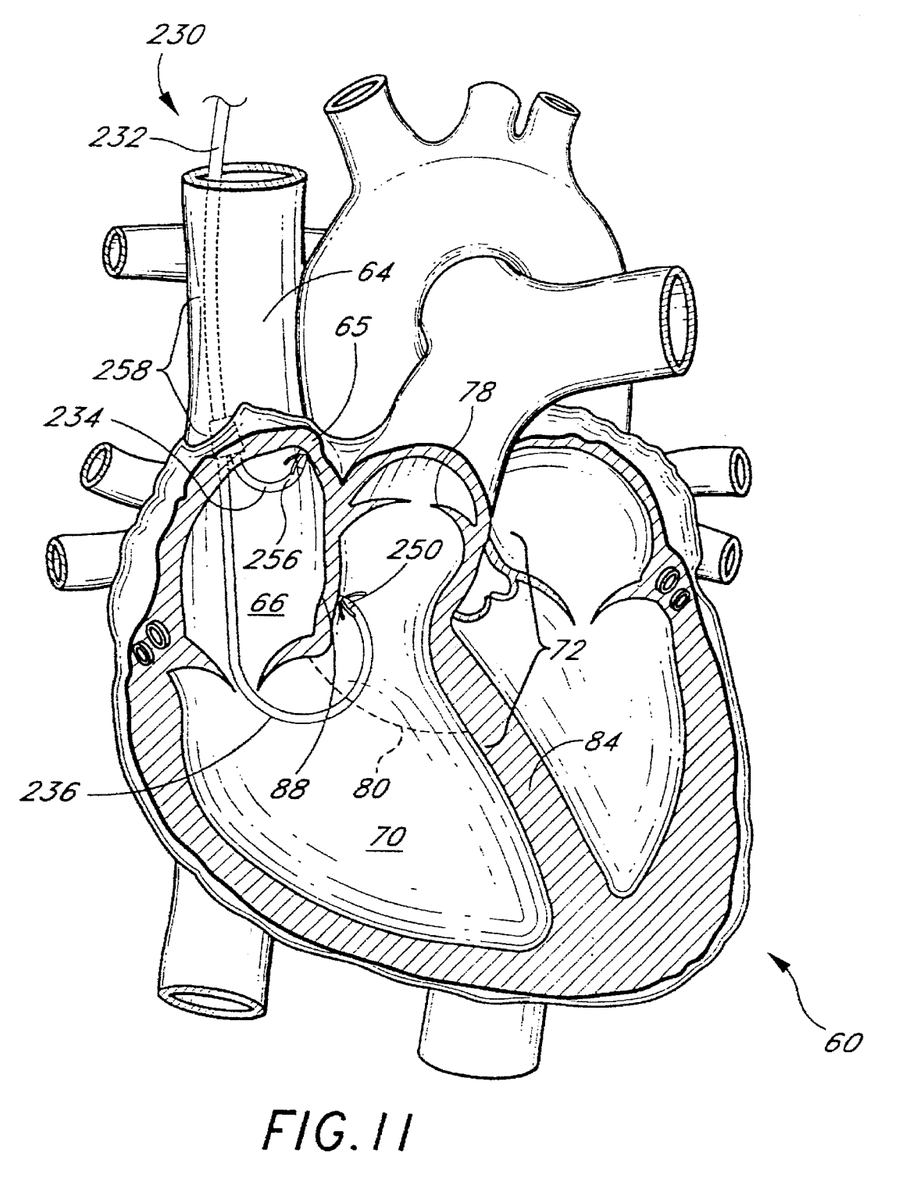
FIG. 11 is a perspective view illustrating the lead of FIG. 9 following implantation within the heart.

FIG. 11 shows the lead 230 following proper implantation within the heart 60, with both stylets 244, 246 fully withdrawn. The lead body 232 passes through the superior vena cava 64, and branches into the separate atrial and ventricular branches 234, 236 just above the right atrium 66. The atrial branch 234 extends laterally and anteriorly across the right atrium 66, with the atrial electrode 256 pressing against the atrial appendage 65. The ventricular branch 236 extends through the right atrium 66, into the right ventricle 70, and upward into the RVOT 72. The RVOT electrode 250 presses against a wall 88 of the RVOT 72 that is proximate to the right atrium 66.

As generally illustrated by FIG. 11, the atrial and ventricular branches 234, 236 are preformed to assume curved, J-shaped configurations upon removal of the respective stylets 244 and 246 (FIG. 9). The preformed atrial branch 234 is configured so as to bias the lead body 232 against the posterior wall of the superior vena cava 64 (in the region shown generally by the reference number 258), while biasing the atrial electrode 256 against the atrial appendage 65. The biasing force generated by the preformed atrial branch 234 is sufficient to maintain the atrial branch 234 in the position shown, and to impede the lead body 232 from sliding within the superior vena cava.

The preformed ventricular branch 236 is configured so as to hook the RVOT electrode 250 into the RVOT 72 and to bias the RVOT electrode 250 against a wall 88 of the RVOT 72 in a direction generally toward the right atrium 66. The biasing forces applied by the atrial electrode 256 against the atrial appendage 65 and by the lead body 232 against the posterior wall of the superior vena cava 64 help to maintain the ventricular branch 236 in the position shown.

Figure 12:
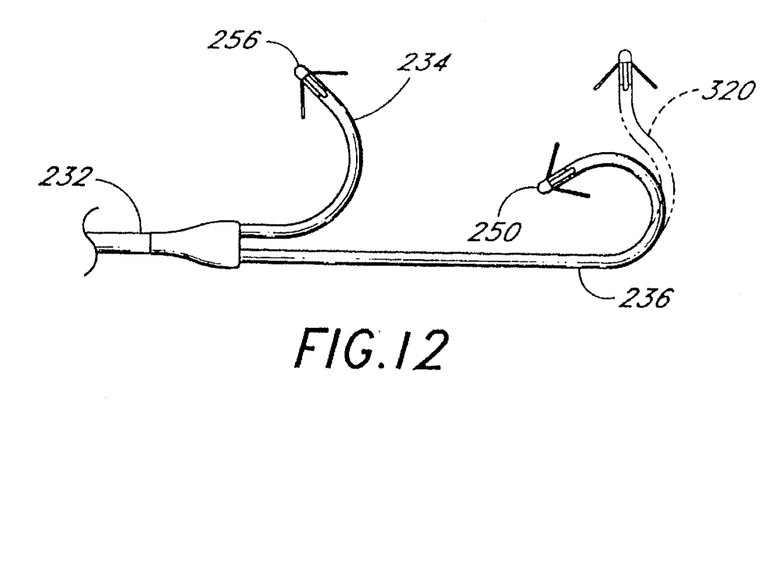
FIG. 12 is a plan view illustrating the configurations of the atrial and ventricular branches of the lead of FIG. 9 when first and second stylets are withdrawn.

FIG. 12 illustrates the configuration of the distal portion of the lead body 232 when the stylets 244 and 246 are removed with the lead 230 in free space. The atrial and ventricular branches 234, 236 assume generally J-shaped configurations, with the direction of curvature being generally the same for each branch. The ventricular branch 236 has a greater curvature than the atrial branch 234, and substantially forms a loop.

Alternative configurations of the atrial and ventricular branches 234, 236 can be used to vary the electrode placement from that shown in FIG. 11. For example, referring to FIG. 12, the ventricular branch 236 can be preformed to assume the configuration shown in phantom and denoted by reference number 320. This would permit the RVOT electrode 250 to be biased against the interventricular septum 84. Alternatively, the distal-most portion of the ventricular branch 236 can be extended in length to permit the RVOT electrode 250 to be positioned just below the pulmonary valve 78.

While various embodiments of single-pass A-V leads in accordance with the present invention have been described, these embodiments have been presented by way of example only, and are not intended to limit the scope of the present invention. Thus, the breadth and scope of the present invention should be defined only in accordance with the following claims and their equivalents.

What is claimed is:

1. A single-pass A-V lead for producing an improved sequence of activation for use in a dual-chamber cardiac pacemaker comprising:

an insulated lead body having a proximal end for connection to a pacemaker and a distal end for placement within the heart, the lead body having at least one lumen adapted for the insertion of a stylet, the lumen extending axially from an exit port at the proximal end;

a right ventricular outflow tract (RVOT) pacing electrode at the distal tip of the lead body and electrically connected to a first conductor that extends within the lead body to the proximal end;

an atrial electrode on the lead body and positioned in spaced relationship to the distal tip, the atrial electrode connected to a second conductor that extends within the lead body to the proximal end; and the lead body comprising a preformed ventricular portion that assumes a curved configuration when the stylet is withdrawn from the lumen, the curvature of the preformed ventricular portion being sufficient to bias the RVOT electrode against a wall of the RVOT so that ventricular stimulation occurs using the RVOT pacing electrode which results in a fastener sequence of activation than apical stimulation.

2. The single-pass A-V lead, as defined in claim 1, wherein the lead body further comprises a preformed atrial portion that forms a laterally projecting bow when the stylet is withdrawn from the lumen, the atrial electrode being located substantially at an outward facing surface of the bow, and wherein the preformed ventricular portion is oriented relative to the preformed atrial portion so as to urge the RVOT electrode generally toward the atrial electrode when the stylet is withdrawn.

3. The single-pass A-V lead, as defined in claim 2, wherein the preformed atrial and ventricular portions are configured such that heart tissue separating the RVOT and right atrium is squeezed between the RVOT and atrial electrodes when the stylet is withdrawn.

4. The single-pass A-V lead, as defined in claim 2, wherein the preformed atrial and ventricular portions are configured such that, when the stylet is withdrawn, the atrial electrode is urged against the interatrial septum and the RVOT electrode is urged against a wall of the RVOT that is adjacent to the aorta.

5. The single-pass A-V lead, as defined in claim 2, wherein the lead body is configured such that, when the stylet is withdrawn, the laterally projecting bow and a major curve of the preformed ventricular portion fall generally within a single plane.

6. The single-pass A-V lead, as defined in claim 2, wherein the lead body is configured such that, when the stylet is withdrawn, the laterally projecting bow falls generally within a first plane, and wherein a major curve of the preformed ventricular portion falls generally within a second plane.

7. The single-pass A-V lead, as defined in claim 6, wherein the first and second planes are rotated between 30 and 90 degrees relative to one another.

8. The single-pass A-V lead, as defined in claim 6, wherein the lead body further comprises an inward bend within a last 1.5 centimeter ventricular portion thereof, the inward bend projecting the RVOT electrode out of the second plane.

9. The single-pass A-V lead, as defined in claim 2, wherein the preformed atrial and ventricular portions are configured to fall generally within respective first and second planes such that heart tissue separating the RVOT and right atrium is squeezed between the RVOT and atrial electrodes when the stylet is withdrawn.

10. The single-pass A-V lead, as defined in claim 2, wherein the distal end of the lead body is unbranched, the atrial electrode is formed in-line with the lead body, and wherein an inward-facing surface of the atrial electrode is coated with an insulating material to prevent discharge of current into the bloodstream.

11. The single-pass A-V lead, as defined in claim 1, wherein the lead body further comprises a preformed atrial portion, and wherein the preformed atrial and ventricular portions are configured so as to urge the RVOT electrode and the atrial electrode in opposing directions when the stylet is withdrawn to thereby generate a biasing force to hold the atrial and RVOT electrodes in position.

12. The single-pass A-V lead, as defined in claim 11, wherein the preformed atrial portion forms a laterally projecting bow when the stylet is withdrawn from the lumen, and wherein the atrial electrode is located substantially at an outwardly facing surface of the bow.

13. The single-pass A-V lead, as defined in claim 11, wherein the preformed atrial and ventricular portions are configured such that the atrial electrode presses against the right atrial free wall of the heart.

14. The single-pass A-V lead, as defined in claim 11, wherein the distal end of the lead body is unbranched, the atrial electrode is formed in-line with the lead body, and wherein an inward-facing surface of the atrial electrode is coated with an insulating material to reduce unnecessary discharge of current into the bloodstream.

15. The single-pass A-V lead, as defined in claim 1 wherein the lead body has an atrial branch and a ventricular branch and has a first lumen adapted for the insertion of a first stylet and a second lumen adapted for the insertion of a second stylet, the first lumen extending axially from a first exit port at the proximal end into the atrial branch and the second lumen extending axially from a second exit port at the proximal end into the ventricular branch, and wherein the atrial electrode is located at the distal tip of the atrial branch and the RVOT electrode is located at the distal tip of the ventricular branch, and wherein the preformed ventricular portion of the lead body is formed in the ventricular branch and assumes the curved configuration when the second stylet is withdrawn from the second lumen.

16. The single-pass A-V lead, as defined in claim 15, wherein the atrial branch comprises a preformed portion that assumes a curved configuration when the first stylet is withdrawn from the atrial branch, the curvature of the preformed portion of the atrial branch being sufficient to bias the atrial electrode against a wall of the right atrium.

17. A single-pass A-V lead for implantation within a human heart, comprising:
  an insulated lead body having a proximal end for connection to a pacemaker and an unbranched distal end for placement within the heart, the lead body having a lumen adapted for the insertion of a stylet, the lumen extending axially from an exit port at the proximal end substantially to the distal end;
  a ventricular electrode at the distal tip of the lead body and electrically connected to a first conductor that extends within the lead body to the proximal end; and
  a curved, atrial electrode formed in-line with the lead body, the atrial electrode located at a prebent, atrial portion of the lead body that forms a laterally projecting bow when the stylet is withdrawn such that the atrial electrode is pressed against a wall of the atrium, and wherein an inward-facing surface of the atrial electrode is coated with an insulating material to reduce discharge of current into the bloodstream and to thereby consume battery life of a pacemaker to which the single-pass A-V lead connects.

18. The single-pass A-V lead, as defined in claim 17, wherein the lead body comprises a prebent ventricular portion adapted to project the ventricular electrode against a wall of the right ventricular outflow tract.

19. The single-pass A-V lead, as defined in claim 18, wherein the prebent ventricular portion forms a loop when the stylet is withdrawn in free space.

20. The single-pass A-V lead, as defined in claim 19, wherein the laterally projecting bow falls generally within a first plane and the loop falls generally within a second plane.

21. The single-pass A-V lead, as defined in claim 20, wherein the first and second planes are rotated between 30 and 90 degrees relative to one another.

22. A single-pass A-V lead for implantation within a human heart, comprising:
  an insulated lead body having a proximal end for connection to a pacemaker and a branched distal end having an atrial branch and a ventricular branch, the lead body having a first lumen adapted for the insertion of a first stylet, the first lumen extending axially from a first exit port at the proximal end into the atrial branch, the lead body also having a second lumen adapted for the insertion of a second stylet, the second lumen extending axially from a second exit port at the proximal end into the atrial branch;
  an atrial electrode on the atrial branch and electrically connected to a first conductor that extends within the lead body to the proximal end;
  means for biasing the atrial electrode against a wall of the right atrium, the means for biasing comprising a preformed portion of the atrial branch that assumes a curved configuration when the first stylet is withdrawn from the atrial branch;
  a right ventricular outflow tract (RVOT) electrode on the ventricular branch and electrically connected to a second conductor that extends within the lead body to the proximal end; and
  means for positioning the RVOT electrode against a wall of the RVOT, the means comprising a preformed portion of the ventricular branch that assumes a curved configuration when the second stylet is withdrawn from the ventricular branch.

23. The single-pass A-V lead, as defined in claim 22, wherein the preformed portion of the atrial branch is configured so as to bias the atrial electrode against the right atrial appendage of the heart.

24. The single-pass A-V lead, as defined in claim 22, wherein the preformed portion of the ventricular branch is configured so as to bias the RVOT electrode against the wall in a direction generally toward the right atrium of the heart.

25. The single-pass A-V lead, as defined in claim 22, wherein the preformed portion of the ventricular branch is configured to substantially form a loop when the second stylet is withdrawn.

26. A method of providing remote electrical access to the right atrium and the right ventricular outflow tract (RVOT) of a human heart using a single-pass A-V lead that has an atrial electrode and a ventricular electrode, the method comprising the steps of:
  (a) positioning the atrial electrode at a location within the right atrium and in contact with an atrial wall;
  (b) positioning the ventricular electrode at a location in the RVOT and in contact with a ventricular wall;
  (c) maintaining the atrial and ventricular electrodes in the locations, respectively by biasing the atrial electrode against the atrial wall with a first force and biasing the ventricular electrode against the ventricular wall with a second force, and applying at least one of the forces using a preformed bend in a section of the lead.

27. The method, as defined in claim 26, wherein the first force and the second force are substantially equal in magnitude and opposite in direction.

28. The method, as defined in claim 26, wherein the step of maintaining comprises applying the first force and the second force to opposing sides of a septal wall that separates the right atrium from the RVOT.

29. The method, as defined in claim 26, wherein the step of maintaining comprises applying the first force to the right atrial free wall and the second force to the interventricular septum.

30. A pacing lead for providing an improved sequence of activation, comprising:
  an insulated lead body having a proximal end for connection to a pacemaker and a distal end for placement within a human heart, the lead body having at least one lumen adapted for the insertion of a stylet, the lumen extending axially from an exit port at the proximal end; and
  a right ventricular outflow tract (RVOT) pacing electrode at the distal tip of the lead body and electrically connected to a conductor that extends within the lead body to the proximal end;
  wherein a ventricular portion of the lead body is preformed to assume a curved configuration when the stylet is withdrawn from the lumen, and wherein the preformed ventricular portion is configured to position the RVOT electrode within the RVOT when the lead is properly implanted within the human heart so that ventricular stimulation occurs using the RVOT pacing electrode which results in a fastener sequence of activation than apical stimulation.

31. A pacing lead, as in claim 30, wherein the preformed ventricular portion is configured to bias the RVOT electrode against a wall of the RVOT when the lead is properly implanted within the human heart.

32. A pacing lead, as in claim 31, further comprising an atrial electrode on an atrial portion of the lead, the atrial portion being preformed to assume a curved configuration when the stylet is withdrawn from the lumen, the atrial portion being configured to bias the atrial electrode against a wall of the right atrium of the heart to thereby generate a counteracting force for biasing the RVOT electrode against the wall of the RVOT.

33. A method of pacing a human heart so as to provide an improved sequence of activation, comprising the steps of:

providing an elongated pacing lead having an electrode at a distal end thereof, the pacing lead having a lumen which extends longitudinally therein to permit the insertion of a stylet, a ventricular portion of the pacing lead being preformed to assume a curved configuration when the stylet is withdrawn from the lumen;

advancing the pacing lead through the venous system of a human with the stylet inserted within the lumen, to position the electrode and the ventricular portion within the right ventricle of the human heart;

withdrawing the stylet from the lumen to allow the ventricular portion to assume the preformed curved configuration, to thereby position the electrode within the right ventricular outflow tract (RVOT) of the heart; and applying an electrical stimulus to the heart within the RVOT via the lead, to thereby induce a ventricular contraction in the region of the RVOT to produce a more rapid sequence of activation.

34. The method, as defined in claim 33, wherein the step of withdrawing comprises biasing the electrode against a wall of the RVOT to thereby maintain the electrode in position within the RVOT.

35. The method, as defined in claim 34, wherein the pacing lead further comprises an atrial electrode on an atrial portion thereof, the atrial portion being preformed to assume a curved configuration when the stylet is withdrawn from the lumen, and wherein the method further comprises the step of biasing the atrial electrode against a wall of the right atrium of the heart to thereby provide a counteracting force the biasing of the electrode against the wall of the RVOT.

* * * * *